United States Patent [19]
Giles et al.

[11] Patent Number: 6,048,983
[45] Date of Patent: Apr. 11, 2000

[54] PROCESS FOR THE PREPARATION OF BENZOPYRAN COMPOUNDS

[75] Inventors: Robert Gordon Giles, Tonbridge; Paul Oxley, Tunbridge Wells, both of United Kingdom

[73] Assignee: SmithKline Beecham pl.c, Brentford, United Kingdom

[21] Appl. No.: 09/242,094

[22] PCT Filed: Aug. 5, 1997

[86] PCT No.: PCT/EP97/04328

§ 371 Date: Feb. 8, 1999

§ 102(e) Date: Feb. 8, 1999

[87] PCT Pub. No.: WO98/06718

PCT Pub. Date: Feb. 19, 1998

[30] Foreign Application Priority Data

Aug. 8, 1996 [GB] United Kingdom .................. 9616629

[51] Int. Cl.$^7$ ..................................................... C07D 257/00
[52] U.S. Cl. .......................................... 548/253; 548/252
[58] Field of Search ..................................... 548/252, 253

[56] References Cited

FOREIGN PATENT DOCUMENTS 0 173 516   3/1986   European Pat. Off. .
2 302 873   2/1997   United Kingdom .

OTHER PUBLICATIONS

Chemical Abstract, vol. 115, No. 17, 1991, Columbus Ohio, abstract No. 182817v, p. 874, XP002048521, see abstract.

Primary Examiner—Deborah C. Lambkin
Attorney, Agent, or Firm—James M Kanagy; Charles M. Kinzig

[57] ABSTRACT

A process for preparing certain substituted benzopyran compounds is disclosed.

6 Claims, No Drawings

PROCESS FOR THE PREPARATION OF BENZOPYRAN COMPOUNDS

This application is a 371 of PCT/EP97/04328 Aug. 5, 1997.

The present invention relates to a process for preparing certain substituted benzopyran compounds which are useful as intermediates in the preparation of a class of substituted benzopyran compounds known in the art as therapeutic agents.

Substituted benzopyran compounds are known in the art. For example EP 0 173 516-A discloses a class of substituted benzopyran compounds which are described as compounds having activity as leukotriene antagonists and 5-α-reductase inhibitors and useful in therapy in the treatment of diseases caused or exacerbated by leukotrienes or 5-α-reductase activity.

Various procedures for preparing such compounds are known in the art but these suffer from certain disadvantages when considered for large scale commercial application. The present invention therefore provides an improved route to substituted benzopyran compounds which gives the desired compounds in good yield with relatively few process steps.

In a first aspect is therefore provided a process for the preparation of a compound of structure (I):

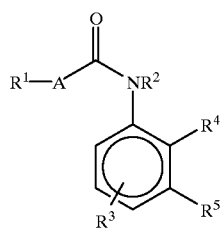
(I)

in which, $R^1$ is $C_{1-20}$akyl, $C_{2-20}$alkenyl, $C_{2-20}$alkynyl, or a group of structure:

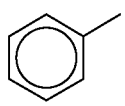
(i)

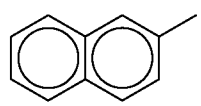
(ii)

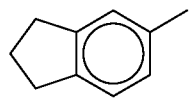
(iii)

each of which may be substituted by one or two substituents selected independently from $C_{1-20}$alkyl, $C_{2-20}$alkenyl or $C_{2-20}$alkynyl, up to 5 carbon atom(s) of which may optionally be replaced by oxygen atom(s), sulphur atom(s), halogen atom(s), nitrogen atom(s), benzene ring(s), thiophene ring(s), naphthalene ring(s), carbocyclic ring(s) of from 4 to 7 carbon atom(s), carbonyl group(s), carbonyloxy group(s), hydroxy group(s), carboxy group(s), azido group(s) and/or nitro group(s);

$R^2$ is hydrogen or $C_{1-6}$alkyl;

$R^3$ is hydrogen, halogen, hydroxy, nitro, a group of general formula —COOR$^6$ (wherein R$^6$ represents hydrogen or $C_{1-6}$alkyl), $C_{1-6}$alkyl, $C_{1-6}$alkoxy or $C_{1-6}$alkylthio; A is a single bond or a vinylene, propenyl-1-ene, butenyl-1-ene, butadienyl-1-ene or ethynylene group optionally being substituted by one, two or three $C_{1-10}$alkyl and/or phenyl group(s); provided that the group formed by $R^1$ and A provides a double or triple bond adjacent to the carbonyl group of the compound of formula (I);

$R^4$ is OH and $R^5$ is COCH$_3$ or $R^4$ and $R^5$ together with the phenyl ring to which they are attached form a substituted benzopyran structure of formula (i):

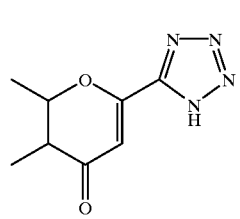
(i)

which comprises reaction of a compound of formula (II):

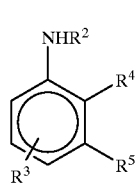
(II)

in which $R^2$, $R^3$, $R^4$ and $R^5$ are as defined in formula (I) with a compound of formula (III):

$R^1$—A—X
(III)

in which $R^1$ and A are as defined in formula (I) and X is a suitable group to allow metal insertion in the presence of a metal catalyst and carbon monoxide, and optionally thereafter, forming a salt or N-oxide
converting the resulting compound of formula (I) into another compound of formula (I)

Suitably the reaction is carried out at elevated temperature in the presence of a metal catalyst. Metal catalysts include the carbonyl complexes of Ni, Rh, Fe and Co or palladium complexes. A particularly advantageous aspect of the use of palladium complexes is that they can be used in catalytic quantities, thereby avoiding the use of highly toxic metal carbonyls, and enabling easier separation of the desired products from metal residues. Suitable palladium catalysts include Pd(OAc)$_2$, (Ph$_3$P)$_4$Pd, (Ph$_3$P)$_2$PdX$_2$ [e.g. X=I,Br, Cl], (bipyr)$_2$Pd, bis(dibenzilidene acetone)Pd(0). The reaction can be carried out in the presence of a reducing agent such as ammonium formate or hydrazine hydrate. Preferably the reaction can be carried out in the presence of additional ligands such as Ph$_3$P, sulphonated-Ph$_3$P, tri-tolylphosphine, bis(diisopropylphosphinyl)propane, polymer-bound-Ph$_2$P, and 1,1'-bis-(diphenylphosphino)ferrocene.

Preferably the reaction is carried out in the presence of a base. Suitable bases include Hunig's base, tri-n-butylamine, DBU, DABCO, or sodium acetate.

Suitably the reaction is carried out in a dipolar aprotic solvent, for example in amidic solvents such as dimethylformamide, N-methyl-pyrrolidinone or dimethylacetamide, or in dimethyl sulphoxide or pyridine. In the case of catalysts with water soluble ligands such as sulphonated-$Ph_3P$ the reaction can be carried out in water.

Suitably X is a group which allows metal insertion, for example halogen or triflate group.

It will be apparent to those skilled in the art that in order for metal insertion to take place, the group formed by $R^1$ and A in compounds of formula (I) must provide a double or triple bond adjacent to the carbonyl group of compounds of formula (I). In other words the carbon atom adjacent to the carbonyl group of compounds of formula (I) must be an $sp^2$ or sp hybridised carbon.

In particular, the reactions claimed herein are useful in the preparation of compounds (I) in which $R^1$ and A form a group of formula (ii):

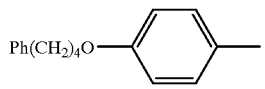
(ii)

Preferably $R^2$ and $R^3$ are both hydrogen.

Preferably $R^4$ and $R^5$ together form a group of formula (i) as defined above such that $R^4$ and $R^5$ together with the phenyl ring to which they are attached form a substituted benzopyran structure. When $R^4$ is OH and $R^5$ is $COCH_3$ the resulting compound of formula (I) can be converted to the compound of formula (I) where $R^4$ and $R^5$ together form a group of formula (i) using the procedure disclosed in WO 94/12492.

Most preferably the process of the invention can be used to prepare the compound Pranlukast, that is to say the compound 4-oxo-8-[4-(4-phenylbutoxy)benzoylamino]-2-(tetrazol-5-yl)-4H-1-benzopyran or salt, hydrate or N-oxide thereof.

Compounds of formula (II) can be prepared by known procedures, for example using the chemistry disclosed in EP 0 173 516-A.

Compounds of formula (III) can be prepared from the corresponding phenols using standard chemistry, for example as shown below:

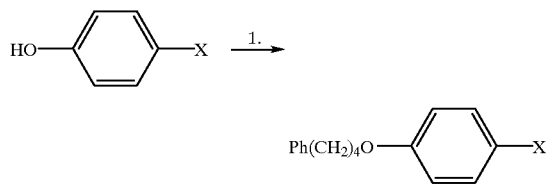

1. $Ph(CH_2)_4Br$, DMF, $K_2CO_3$, heat.

The following examples serve to illustrate the invention. Preparation of 4-(4-phenylbutoxy)halobenzene Derivatives

EXAMPLE 1

Preparation of 4-(4-Phenylbutoxy)bromobenzene

Potassium carbonate (7.6 g, 55.1 mmole), 4-bromophenol (5 g, 28.9 mmole) and 4-phenylbutylbromide (5.7 g, 26.8 mmole) were stirred in dimethylformamide (30 ml) and heated at 100° C. for two hours. The reaction mixture was quenched into water (150 ml) and the aqueous phase extracted with ether (2×75 ml). The combined ethereal extracts was washed with sodium hydroxide solution (~0.5 M, 120 ml) and water (100 ml). The organic layer was dried over sodium sulphate, filtered, and concentrated in vacuo to an oil.

The crude product was purified using column chromatography (Stationary phase: silica; Eluent: petroleum ether (60/80) and then 9:1 (v/v) petroleum ether (60/80): dichloromethane) to give 4-(4-phenylbutoxy)bromobenzene (5.78 g, 71%).

NMR ($CDCl_3$) ppm, 1.72–1.82, 4H, m; 2.11–2.67, 2H, m; 3.85–3.89, 2H, m; 6.71, 2H, d; 7.14, 5H, m; 7.31, 2H, d.

MS (E.I.) m/z (%) 65 (18), 91 (100), 104 (15), 117 (10), 132 (17), 172 (16), 304 (3).

EXAMPLE 2

Preparation of 4-(4-phenylbutoxy)iodobenzene

Using the preparative procedure for 4-(4-phenylbutoxy) bromobenzene, except using 4-iodophenol in place of 4-bromophenol, gave 4-(4phenylbutoxy)iodobenzene in 80% yield.

NMR ($CDCl_3$) ppm, 1.70–1.77, 4H, m; 2.61–2.66, 2H, m; 3.81–3.86, 2H, m; 6.59, 2H, d; 7.11–7.28, 5H, m; 7.48, 2H, d.

MS (E.I.) m/z (%) 65 (12, 91 (100), 104 (8), 132 (8), 220 (35), 352 (6).

Carbonylation Procedure 1. Preparation of 8-amido-4-oxo-2-(tetrazol-5-yl)-4H-1-benzopyran Derivatives

EXAMPLE 3a

Preparation of 4-Oxo-8-[4-(4-phenylbutoxy) benzoylamino]-2-(tetrazol-5-yl)-4H-1-benzopyran Hemihydrate A mixture of 4-(4-phenylbutoxy)bromobenzene (0.50 g, 1.64 mmole), 8-amino-4-oxo-2-(tetrazol-5-yl)-4H-1-benzopyran (0.75 g, 3.28 mmole), bis-(triphenylphospine) palladium (II) chloride (0.135 g, 0.19 mmole) and 1,8-diazabicyclo[5.4.0]undec-7-ene (0.87 g, 5.74 mmole) was stirred in N-methylpyrrolidinone (10 ml) at 100–110° C. under an atmosphere of carbon monoxide at atmospheric pressure for 4.5 hours. The reaction mixture was diluted with water (15 ml) and acidified using concentrated hydrochloric acid (5 ml). The precipitate was filtered, washed with water and methanol and then stirred in concentrated hydrochloric acid (8 ml) to dissolve unreacted 8-amino-4-oxo-2-(tetrazol-5-yl)-4H-1-benzopyran. The undissolved solid was filtered, washed with concentrated hydrochloric (2×1.5 ml), water, then methanol. The damp cake was stirred with sodium acetate (0.15 g, 1.83 mmole) in methanol (10 ml) and the solution filtered. The supernatant liquor was acidified with concentrated hydrochloric acid (0.2 ml), and the product filtered, washed with methanol and dried to give the title compound (422 mg, 53%).

NMR (DMSO-$d_6$) ppm, 1.70–1.86, 4H, m; 2.66–2.71, 2H, m; 4.10–4.14, 2H, m; 7.09, 2H, d; 7.10, 1H, s; 7.18–7.33, 5H, m; 7.57, 1H, dd; 7.90, 1H, dd; 8.03, 2H, d; 829, 1H, dd; 9.97, 1H, s.

MS (positive ion ionspray) m/z (%) 107 (100), 126, (10), 169 (13), 482 (97), 963 (40).

MS (negative ion ionspray) m/z (%) 452 (11), 480 (100), 961 (10).

EXAMPLE 3b

Repeating carbonylation procedure 1 using 4-(4-phenylbutoxy)iodobenzene in place of 4-(4'-phenylbutoxy) bromobenzene gave the title compound in 55% yield.

EXAMPLE 4a

Preparation of 6-chloro-4-oxo-8-[4-(4-phenylbutoxy)benzoylamino]-2-(tetrazol-5-yl)-4H-1-benzopyran Repeating carbonylation procedure 1 using 8-amino-6-chloro-4-oxo-2-(tetrazol-5-yl)-4H-1-benzopyran in place of 8-amino-4-oxo-2-(tetrazol-5-yl)-4H-1-benzopyran gave 6-chloro-4-oxo-8-[4-(4-phenylbutoxy)benzoylamino]-2-(tetrazol-5-yl)-4H-1-benzopyran in 10% yield.

NMR (DMSO-$d_6$) ppm, 1.73–1.79, 4H, m; 2.64–2.70, 2H, m; 4.09, 2H, m; 7.10, 2H, d; 7.15, 6H, m ; 7.80, 1H, d; 8.01, 1H, d; 8.43, 2H, d; 10.02, 1H, s.

MS (positive ion ionspray) m/z (%) 516 (100).

MS (negative ion ionspray) m/z (%) 514 (100), 1029 (3).

EXAMPLE 4b

Repeating carbonylation procedure 1 using 8-amino-6-chloro4-oxo-2-(tetrazol-5-yl)-4H-1-benzopyran and 4-(4-phenylbutoxy)iodobenzene in place of 8-amino-4-oxo-2-(tetazol-5-yl)-4H-1-benzopyran and 4-(4-phenylbutoxy)bromobenzene, gave 6-chloro-4-oxo-8-[4-(4-phenylbutoxy)benzoylamino]-2-(tetrazol-5-yl)4H-1-benzopyran in 92% yield.

Carbonylation Procedure 2. Preparation of 3-benzamido-2-hydroxyacetophenone Derivatives

EXAMPLE 5a

Preparation of 5-chloro-3-[4-(4-phenylbutoxy)benzoylamino]-2-hydroxy Acetophenone 4-(4-Phenylbutoxy)bromobenzene (0.50 g, 1.64 mmole), 5-chloro-3-amino-2-hydroxyacetophenone (0.53 g, 2.89 mmole), bis(triphenylphosphine)palladium (II) chloride (0.10 g, 0.14 mmole) and 1,8-diazabicyclo[5.4.0]undec-7ene (0.87 g, 5.74 mmole) was stirred in N-methylpyrrolidinone (10 ml) at 100–110° C. under an atmosphere of carbon monoxide at atmospheric pressure for 1.75 hours. The reaction mixture was cooled, quenched into water (50 ml) containing concentrated hydrochloric acid (5 ml) and extracted with dichloromethane (50 ml and 2×25 ml). The combined extracts were treated with charcoal, dried (MgSO$_4$), concentrated in vacuo and the crude product stirred in isopropanol (30 ml) at 0–5° C. The precipitate was filtered, washed with chilled isopropanol and dried to give 5-chloro-3-[4-(4-phenylbutoxy)benzoylamino]-2-hydroxyacetophenone (0.52 g, 72%).

NMR (CDCl$_3$) ppm, 1.76–1.91, 4H, m ; 2.65, 3H, s; 2.68–2.73, 2H, m; 4.01–4.06, 2H, m; 6.96, 2H, d; 7.16–7.34, 5H, m; 7.43, 1H, d; 7.85, 2H, d; 8.57, 1H, s; 8.83, 1H, d; 12.90, 1H, s.

MS (positive ion ionspray) m/z [M+H]$^+$ 438.

MS (negative ion ionspray) m/z [M–H]$^-$ 436.

EXAMPLE 5b

Repeating carbonylation procedure 2 using 4-(4-phenylbutoxy)iodobenzene in place of 4-(4phenylbutoxy)bromobenzene gave 5-chloro-3-[4-(4-phenylbutoxy)benzoylamino]-2-hydroxyacetophenone in 82% yield.

EXAMPLE 6

Preparation of 3-[4-(4-phenylbutoxy)benzoylamino]-2-hydroxyacetophenone

Repeating carbonylation procedure 2 using 3-amino-2-hydroxyacetophenone and 4-(4-phenylbutoxy)iodobenzene in place of 3-amino-5-chloro-2-hydroxy acetophenone and 4-(4-phenylbutoxy)bromobenzene, gave 3-[4-(4-phenylbutoxy)benzoylamino]-2-hydroxyacetophenone in 68% yield.

NMR (CDCl$_3$) ppm, 1.78–1.88, 4H, m; 2.66, 3H, s; 2.66–2.73, 2H, m; 4.01–4.05, 2H, m; 6.93–6.99, 3H, m; 7.16–7.33, 5H, m; 7.48, 1H, dd; 7.87, 2H, d; 8.58, 1H, s; 8.76, 1H, dd; 12.98, 1H, s.

MS (positive ion ionspray) m/z [M+H]$^+$ 404.

MS (negative ion ionspray) m/z [M–H]$^-$ 402.

We claim:

1. A process for the preparation of a compound of structure (I):

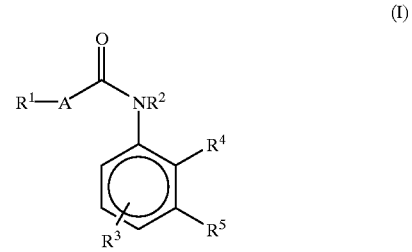

(I)

in which, $R^1$ is $C_{1-20}$alkyl, $C_{2-20}$alkenyl, $C_{2-20}$alkynyl, or a group of structure:

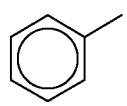

(i)

(ii)

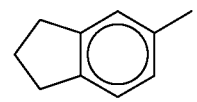

(iii)

each of which may be substituted by one or two substituents selected independently from $C_{1-20}$alkyl, $C_{2-20}$alkenyl or $C_{2-20}$alkynyl, up to 5 carbon atom(s) of which may optionally be replaced by oxygen atom(s), sulphur atom(s), halogen atom(s), nitrogen atom(s), benzene ring(s), thiophene ring(s), naphthalene ring(s), carbocyclic ring(s) of from 4 to 7 carbon atom(s), carbonyl group(s), carbonyloxy group(s), hydroxy group(s), carboxy group(s), azido group(s) and/or nitro group(s);

$R^2$ is hydrogen or $C_{1-6}$alkyl;

$R^3$ is hydrogen, halogen, hydroxy, nitro, a group of general formula —COOR$^6$ (wherein $R^6$ represents hydrogen or $C_{1-6}$alkyl), $C_{1-6}$alkyl, $C_{1-6}$alkoxy or $C_{1-6}$alkylthio;

A is a single bond or a vinylene, propenyl-1-ene, butenyl-1-ene, butadienyl-1-ene or ethynylene group optionally being substituted by one, two or three $C_{1-10}$alkyl and/or phenyl group(s); provided that the group formed by $R^1$ and A provides a double or triple bond adjacent to the carbonyl group of the compound of formula (I);

$R^4$ is OH and $R^5$ is $COCH_3$ or $R^4$ and $R^5$ together form a group of formula (i):

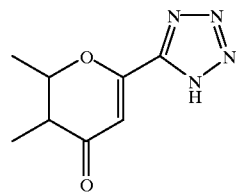 (i)

which comprises reaction of a compound of formula (II):

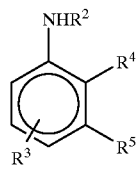 (II)

in which $R^2$, $R^3$, $R^4$ and $R^5$ are as defined in formula (I) with a compound of formula (III):

R¹—A—X  (III)

in which $R^1$ and A are as defined in formula (I) and X is halogen or a triflate group, and optionally thereafter, forming a salt or N-oxide.

2. A process according to claim 1 in which the catalyst is a palladium catalyst.

3. A process claim 1 in which $R^1$ and A form a group of formula (ii):

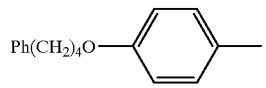 (ii)

4. A process according to claim 1 in which $R^4$ and $R^5$ together form a group of formula (i):

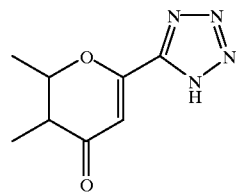 (i)

5. A process according to claim 1 in which the compound prepared is 4-oxo-8-[4-(4-phenylbutoxy)benzoylamino]-2-(tetrazol-5-yl)-4H-1-benzopyran or salt, hydrate or N-oxide thereof.

6. A process according claim 1 in which the compound prepared is 3-[4-(phenylbutoxy)benzoylamino]-2-hydroxy-acetophenone.

* * * * *